United States Patent [19]

Walls, Jr.

[11] Patent Number: 4,936,902
[45] Date of Patent: Jun. 26, 1990

[54] SELECTIVE CONTROL OF SICKLEPOD IN THE PRESENCE OF LEGUMINOUS CROPS

[75] Inventor: Frank R. Walls, Jr., Wayne, N.C.

[73] Assignee: American Cyanamid Company, Stamford, Conn.

[21] Appl. No.: 343,541

[22] Filed: Apr. 25, 1989

[51] Int. Cl.$^5$ ............................................. A01N 43/48
[52] U.S. Cl. ...................................................... 71/92
[58] Field of Search ............................................ 71/92

[56] References Cited

U.S. PATENT DOCUMENTS

| | | | |
|---|---|---|---|
| 4,371,390 | 2/1983 | Le Clair et al. | 71/DIG. 1 |
| 4,638,068 | 0/0000 | Los. | |
| 4,798,619 | 1/1989 | Los | 71/92 |
| 4,816,060 | 3/1989 | Steller et al. | 71/92 |

Primary Examiner—Glennon H. Hollrah
Assistant Examiner—Eric J. Kraus
Attorney, Agent, or Firm—John W. Hogan, Jr.

[57] ABSTRACT

There is provided a method for the control of sicklepod (Cassia obtusifolia L.) in the presence of leguminous crops. More particularly, this invention provides a method for the selective control of sicklepod in the presence of bean plants by applying to the foliage of said sicklepod a herbicidally effective amount of 2-(4-isopropyl-4-methyl-5-oxo-2-imidazolin-2-yl)-5-methylnicotinic acid.

4 Claims, No Drawings

SELECTIVE CONTROL OF SICKLEPOD IN THE PRESENCE OF LEGUMINOUS CROPS

BACKGROUND OF THE INVENTION 2-(2-Imidazolin-2-yl)pyridines and quinolines and their use as herbicidal agents are described in U.S. Pat. Nos. 4,638,068 issued Jan. 20, 1987 and 4,798,619 issued Jan. 17, 1989. These patents describe processes for the preparation of compounds having the structure:

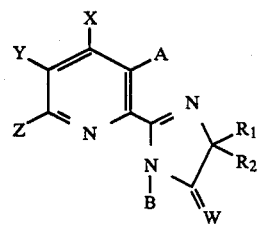

wherein A, B, $R_1$, $R_2$, W, X, Y and Z represent a wide variety of substituents and demonstrate pre-emergence and post-emergence herbicidal activity for more than three hundred of such imidazolinone pyridines and quinolines. The patents specifically disclose the compound 2-(4-isopropyl-4-methyl-5-oxo-2-imidazolin-2-yl)-5-methylnicotinic acid and demonstrate the herbicidal activity thereof against a variety of weed species. U.S. Pat. Nos. 4,638,068 and 4,798,619 do not disclose or suggest that 2-(2-imidazolin-2-yl)pyridines and quinolines are active against leguminous weed species (e.g. *Cassia obtusifolia* L. or *Cassia nictitans*, L.) either alone or in the presence of a leguminous crop.

SUMMARY OF THE INVENTION

This invention relates to a method for the selective control of leguminous weeds in the presence of leguminous crops comprising applying to the foliage and stems of said leguminous weeds herbicidally effective amount of 2-(4-isopropyl-4-methyl-5-oxo-2-imidazolin-2-yl)-5-methylnicotinic acid.

Surprisingly, it has now been discovered that one imidazolinone out of the three hundred or more imidazolinones disclosed in U.S. Pat. Nos. 4,638,068 and 4,798,619; namely the compound: 2-(4-isopropyl-4-methyl-5-oxo-2-imidazolin-2-yl)-5-methylnicotinic acid, is unique in its ability to selectively control leguminous weed species in the presence of certain leguminous bean crops. More particularly, it has been found that the compound 2-(4-isopropyl-4-methyl-5-oxo-2-imidazolin-2-yl)-5-methylnicotinic acid can be applied as a post emergent herbicidal agent to established sicklepod (*Cassia obtusifolia* L.) plants growing in the presence of soybeans (*Glycine max*) to control the sicklepod without producing significant injury to the soybeans. This unique selective herbicidal activity of the above-said compound allows control of bean family weed species in the presence of crop plants of the bean family, without significantly injurying said crop plants. Moreover, this unusual activity establishes the compound 2-(4-isopropyl-4-methyl-5-oxo-2-imidazolin-2-yl)-5-methylnicotinic acid as unique amongst imidazolinones.

DESCRIPTION OF THE PREFERRED EMBODIMENTS

In one embodiment, the present invention provides a method for controlling sicklepod in the presence of soybeans by applying to said sicklepod when it is in at least the second true leaf stage of growth, about 0.057 kg/ha to about 0.22 kg/ha of 2-(4-isopropyl-4-methyl-5-oxo-2-imidazolin-2-yl)-5-methyl-nicotinic acid. When the sicklepod and the soybeans are well established and both are about 30 to 45 centimeters in height, the application to said plants of about 0.56 kg/ha to about 1.12 kg/ha and preferably about 0.75 kg/ha to about 1.12 kg/ha of 2-(4-isopropyl-4-methyl-5-oxo-2-imidazolin-2-yl)-5-methylnicotinic acid is effective for reducing and/or eliminating the stand of sicklepod without significantly injuring the soybean crop.

For use in method of the present invention 2-(4-isopropyl-4-methyl-5-oxo-2-imidazolin-2-yl)-5-methylnicotinic acid is usually prepared as aqueous urea solution comprising about 15% to 25% by weight of 2-(4-isopropyl-4-methyl-5-oxo-2-imidazolin-2-yl)-5-methylnicotinic acid; about 0.05% to 1.0% by weight of acetic acid; about 3.0% to 7.0% ammonium hydroxide, aqueous ($NH_3$ 29%); about 15% to 25% by weight of urea and q.s. to 100% with water, which is usually about 45% to 60% by weight of water. Silicone antifoam agent may also be included in the formulation in a concentration of from 0 to about 0.2%.

A typical 2 pound per gallon aqueous solution of the above-identified imidazolinone may have the following compositions:

| Component | W/W % |
|---|---|
| 2-(4-isopropyl-4-methyl-5-oxo-2-imidazolin-2-yl)-5-methylnicotinic acid (95% purity) | 23.7 |
| Aqueous ammonium hydroxide | 5.7 |
| Urea | 15.0 |
| Water | 54.8 |
| Acetic acid | 0.7 |
| 30% silicone emulsion antifoam | 0.1 |
| Total | 100.0% |

In the field the above-identified formulation, which is a 2 pound per gallon 2-(4-isopropyl-4-methyl-5-oxo-2-imidazolin-2-yl)-5-methylnicotinic aqueous solution with urea, is usually diluted with a sufficient amount of water to yield the desired concentrate of the active ingredient in the aqueous spray. A surface active agent may be added to the diluted formulation for spray application. The surfactant if added is usually employed at a concentration between about 0.20% and 0.30% by weight of the finished dilute formulation.

Among the nonionic surfactants that can be used in the diluted formulations of this invention are octylphenoxy polyethoxy ethanol, alkylaryl polyether alcohols, alkylaryl polyoxyethylene glycol, nonylphenoxy polyethoxy ethanol and the like.

Typically the 2-(4-isopropyl-4-methyl-5-oxo-2-imidazolin-2-yl)-5-methylnicotinic acid or its aqueous ammonium salt is employed, but other salts or esters of the acid may be used in accordance with the present invention.

The invention is further illustrated by the following non-limiting examples.

EXAMPLE 1

Preparation of
2-(4-isopropyl-4-methyl-5-oxo-2-imidazolin-2-yl)-5-methylnicotinic acid aqueous solution with urea This formulation is prepared by introducing about 49.32 parts by weight of the water into a kettle and dissolving therein 5.7 parts by weight of aqueous ammonium hydroxide and 15 parts by weight of urea. The mixture is stirred and 0.1 part by weight of silicone antifoam agent is dispersed therein. The pH of the mixture is then adjusted with acetic acid, preferably glacial acetic acid, to between 6.5 and 8.0, preferably about 7.2 and 5.48 parts by weight of water added to provide the 2 pound per gallon imidazolinone aqueous solution with urea.

EXAMPLE 2

Evaluation of
2-(4-isopropyl-4-methyl-5-oxo-2-imidazolin-2-yl)-5-methylnicotinic acid for control of Sicklepod (*Cassia obtusifolia* L.) in the presence of soybeans (*Glycine max* (L) Merr)

In this evaluation the 2 pound per gallon aqueous solution of the imidazolinone with urea described in Example 1 is dissolved in tap water in sufficient amount to provide from 0.057 kg/ha to 0.22 kg/ha of said imidazolinone when the dilute aqueous solutions are applied as liquid sprays to fieldgrown sicklepod in the presence of soybeans at the rate of about 188 liters per hectare. The sicklepod and the soybeans are at the second true leaf stage of growth at the time of spraying. A $CO_2$ back pack sprayer is used and 0.25% by weight of a nonionic octylphenoxy polyethoxy ethanol is added to the diluted formulations in the tank. The plots are randomly selected and sprayed with the selected solution for evaluation. Each plot is approximately 4 meters wide and 30 meters long with soybeans planted in rows on 91 cm centers. The sprayed plots are examined at intervals throughout the growing season and evaluated 3 weeks after treatment using a rating system of 7 to 100%; 0%=no weed control, 100%=complete weed control. Data for sicklepod control and soybean retardation are reported below for the treatment rates used. After rating, the plants are permitted to grow to yield and the various treatments are reported below in Tables I and IA.

TABLE I

Evaluation of 2-(4-isopropyl-4-methyl-5-oxo-2-imidazolin-2-yl)-5-methylnicotinic acid for control of sicklepod in the presence of soybeans

| Active Ingredient | Rate kg/ha | % Control of Sicklepod | % Retardation of Soybeans |
|---|---|---|---|
| 2-(4-isopropyl-4-methyl-5-oxo-2-imidazolin-2-yl)-5-methylnicotinic acid | 0.22 | 90 | 20 |
|  | 0.11 | 80 | 20 |
|  | 0.057 | 75 | 20 |
| Unteated control | 0.0 | 0 | 0 |

TABLE I-A

| Active Ingredient | Rate kg/ha | Soybean Yield kg/ha |
|---|---|---|
| 2-(4-isopropyl-4-methyl-5-oxo-2-imidazolin-2-yl)-5-methylnicotinic acid | 0.22 | 42.3 |
|  | 0.11 | 39.7 |
|  | 0.057 | 40.9 |
| Untreated control | 0.0 | 32.3 |

EXAMPLE 3

Evaluation of
2-(4-isopropyl-4-methyl-5-oxo-2-imidazolin-2-yl)-5-methylnicotinic acid for controlling well established sicklepod (30 centimeters to 45 centimeters in height) in the presence of soybean plants of essentially the same size and maturity.

In these tests, soybean plants approximately 30 to 45 centimeters in height, growing in rows approximately 30 meters in length and on 91 centimeter centers and very heavily infested between rows with mature sicklepod approximately 30 to 45 centimeters in height, are sprayed with aqueous solutions of 2-(4-isopropyl-4-methyl-5-oxo-2-imidazolin-2-yl)-5-methylnicotinic acid prepared as described in Example 1 above and diluted with a sufficient quantity of water to provide from 0.84 kg/ha to 1.12 kg/ha of the above-said imidazolinone when the dilute solutions are applied at the rate of 195 liters per hectare. Seventeen days after treatment the plots are examined and essentially 100% control of the sicklepod is observed with little or no injury to the soybeans.

What is claimed is:

1. A method for the selective postemergence control of sicklepod in the presence of soybeans comprising applying to the foliage and stems of said sicklepod weeds a herbicidally effective amount of 2-(4-isopropyl-4-methyl-5-oxo-2-imidazolin-2-yl)-5-methylnicotinic acid or esters or salts thereof.

2. The method according to claim 1 wherein the sicklepod and the soybean plants are both at the second true leaf stage and the 2-(4-isopropyl-4-methyl-5-oxo-2-imidazolin-2-yl)-5-methylnicotinic acid, ester or salt is applied to the foliage of said plants in the form of an aqueous spray which provides said plants with about 0.057 kg/ka to 0.22 kg/ka of said 2-(4-isopropyl-4-methyl-5-oxo-2-imidazolin-2-yl)-5-methylnicotinic acid, ester or salt.

3. The method according to claim 1 wherein the sicklepod and soybeans are well established plants about 30 centimeters or more in height and the 2-(4-isopropyl-4-methyl-5-oxo-2-imidazolin-2-yl)-5-methylnicotinic acid, ester or salt is applied to the foliage of said plants in the form of an aqueous spray that provides said plants with about 0.56 kg/ka to 1.12 kg/ka of said 2-(4-isopropyl-4-methyl-5-oxo-2-imidazolin-2-yl)-5-methylnicotinic acid, ester or salt.

4. The method according to claim 1 wherein the aqueous ammonium salt of 2-(4-isopropyl-4-methyl-5-oxo-2-imidazolin-2-yl)-5-methylnicotinic acid is applied.

* * * * *